United States Patent [19]

Hammerstrom et al.

[11] 4,053,516
[45] Oct. 11, 1977

[54] PROCESS FOR THE CONTINUOUS PREPARATION OF TETRAMETHYLETHYLENE-DIAMINE

[75] Inventors: Knut Hammerstrom, Cologne; Georg Spielberger, Leverkusen, both of Germany

[73] Assignee: Bayer Aktiengesellschaft, Leverkusen, Germany

[21] Appl. No.: 631,260

[22] Filed: Nov. 12, 1975

[30] Foreign Application Priority Data

Nov. 25, 1974 Germany ............................ 2455678

[51] Int. Cl.² .............................................. C07C 85/04
[52] U.S. Cl. ............................ 260/585 A; 260/583 N
[58] Field of Search ....................... 260/585 A, 583 N

[56] References Cited

U.S. PATENT DOCUMENTS 3,542,876  11/1970  Blaney ............................ 260/585 A
3,728,393  4/1973  Gaige et al. ..................... 260/585 A

FOREIGN PATENT DOCUMENTS 676,331  5/1939  Germany ......................... 260/585 A Primary Examiner—Daniel E. Wyman
Assistant Examiner—John J. Doll
Attorney, Agent, or Firm—Burgess, Dinklage & Sprung

[57] ABSTRACT

Tetramethylethylenediamine is prepared by reacting 1,2-dichloroethane with an excess of dimethylamine at elevated temperatures and pressures. The process is carried out continuously in the presence of water and the amines in the reaction product are liberated by treatment with bases. Unconverted dimethylamine is separated and treated with water and then recycled into the reaction.

8 Claims, 1 Drawing Figure

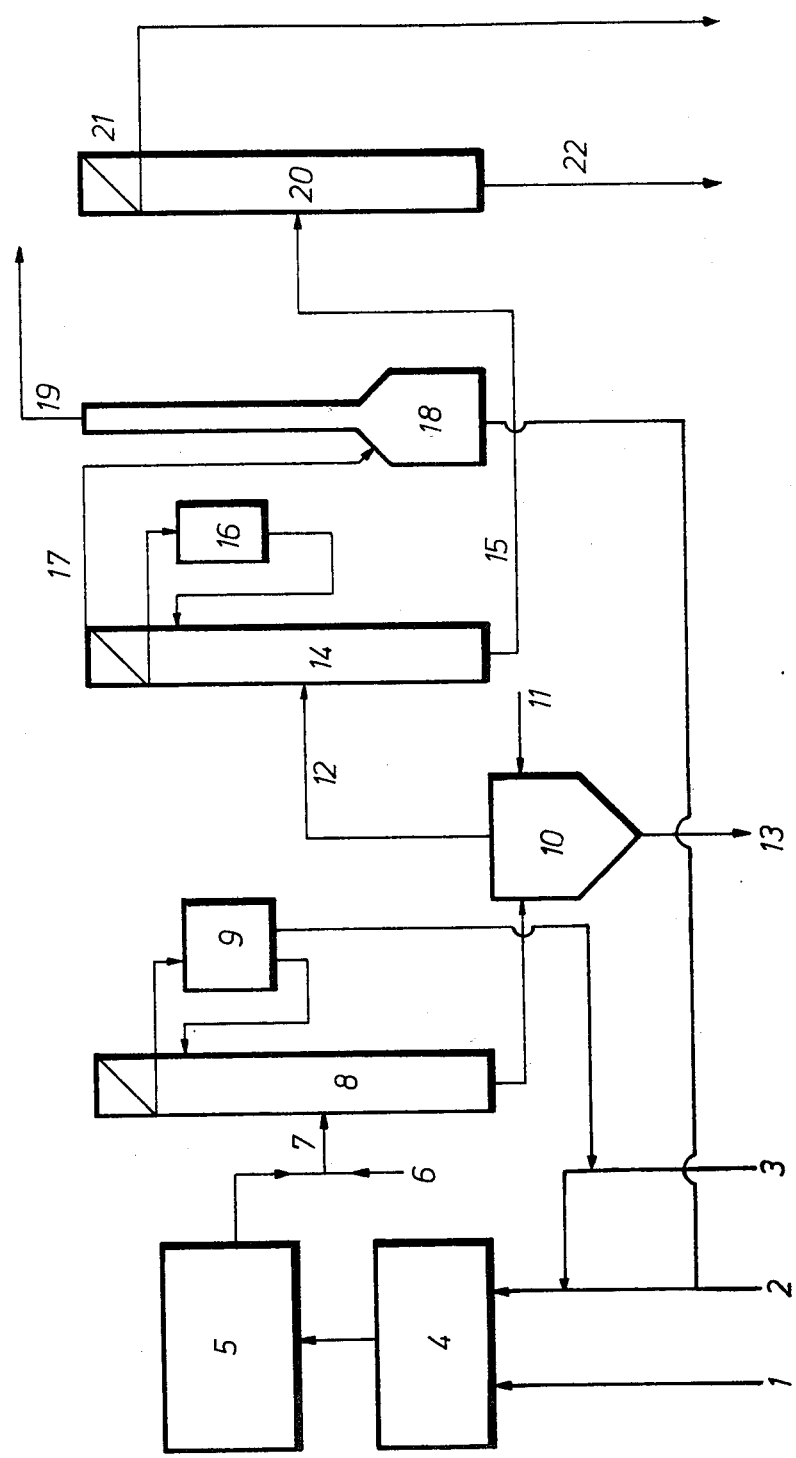

PROCESS FOR THE CONTINUOUS PREPARATION OF TETRAMETHYLETHYLENE-DIAMINE

The invention relates to a process for the continuous preparation of tetramethylethylenediamine.

It is known to prepare tetramethylethylenediamine in a discontinuous process by reaction of 1,2-dichloroethane with an excess of anhydrous dimethylamine (German Pat. No. 676,331).

SUMMARY

According to the present invention, tetramethylethylenediamine is prepared by reacting 1,2-dichloroethane in a continuous process with an excess of dimethylamine at elevated temperature and elevated pressure in the presence of water, treating the reaction product with a base to liberate amines and separating off the unconverted dimethylamine, treating it with water and recycling it to the reaction.

DESCRIPTION

The preparation of tetramethylethylenediamine by the process according to the invention is generally carried out by reacting dimethylamine and ethylene chloride in the presence of water at temperatures of 130° to 200° C, preferably of 150° to 180° C, and pressures of 80 to 120 bars, preferably of 90 to 100 bars. With advantage, the dimethylamine employed, and the water, are warmed, prior to the reaction, to 140° – 160° C, preferably 145° – 155° C, and passed into a mixing chamber for mixing with the ethylene chloride.

In general, the process according to the invention is carried out at a rate of 600 to 800 kg, preferably 650 to 750 kg, of water, relative to 800 to 1,000 kg, preferably 850 to 950 kg, of dimethylamine and 150 to 350 kg, preferably 200 to 300 kg, of ethylene chloride, per hour.

The reaction product essentially consists of tetramethylethylenediamine, unconverted dimethylamine, water and slight impurities. The amines are in part present as hydrochlorides.

After completion of the reaction, the reaction product is, for example, let down into a column into which 20 to 100 l, preferably 40 to 80 l, of concentrated aqueous alkali metal hydroxide solution, for example sodium hydroxide solution, are also introduced.

At the top of the column, dimethylamine can be withdrawn at 8 to 20 bars, preferably 9 to 13 bars, and in part be recycled to the reaction. The amines are liberated completely by further addition of concentrated aqueous alkali metal hydroxide solution to the bottom product of the column.

In a further column, a separation into a bottom product consisting of water and tetramethylethylenediamine and a vapour mixture (top product) consisting of dimethylamine, water and tetramethylethylenediamine can be effected under normal pressure. Thereafter, the vapour mixture can be separated, in the condenser, into a liquid phase (saturated dimethylamine solution in water and tetramethylethylenediamine) and a vapour phase (uncondensed dimethylamine). According to the process of the invention, the liquid phase can be fed into the column as reflux, whilst the uncondensed stream of vapour is treated with water in a further process step, and the dimethylamine is recycled to the reaction as an aqueous solution. The treatment with water can be effected by passing the dimethylamine vapour into water, for example in an absorption system.

The purification of the tetramethylethylenediamine contained in the bottom product of the column can be effected in a further column. By means of this column, the tetramethylethylenediamine is obtained at the top at 95° C as a 68% strength azeotrope with water. The bottom of the column essentially contains the bulk of the water employed for the reaction.

DESCRIPTION OF THE DRAWING

An embodiment of the process according to the invention will be explained, by way of example, in relation to the drawing.

The ethylene chloride 1, the water 2 and the dimethylamine 3 are passed into the mixing chamber 4 and then into the reactor 5. After completion of the reaction, the reaction product is let down via the feed line 7 into a pressure column 8 into which concentrated aqueous alkali metal hydroxide solution 6 is also charged. Dimethylamine is withdrawn at the top of the column and recycled, via the receiver 9, partially as reflux into the column 8 and partially into the reaction 3.

The bottom product of the column 8 is passed into the vessel 10, where the amines are liberated completely by addition of concentrated aqueous alkali metal hydroxide solution 11. The alkali metal chloride produced when liberating the amines is separated off via 13.

The tetramethylethylenediamine, dimethylamine and water which escape as vapour from 10 are passed via the vapour pipe 12 into the column 14. The off-gas 17 obtained on separation in the column 14 and essentially consisting of dimethylamine is passed through water in a subsequent absorption system 18. The dimethylamine which is taken up by the water is admixed to the starting compounds.

2. The unabsorbed by-products are separated off via 19.

The condensate 16 consisting of dimethylamine, water and tetramethylethylenediamine is fed as reflux into the column 14.

The bottom product of the column 14 is passed into a further column 20 and separated. An azeotrope of tetramethylenediamine and water is obtained as the top product 21. The bottom 22 essentially only contains water.

It is surprising that by the process according to the invention it is possible to transfer the discontinuous preparation of tetramethylethylenediamine to continuous preparation with recycle of the unconverted dimethylamine, since the recycled material necessarily carries with it reaction products which lead to the formation of a tarry mass.

The process according to the invention has the advantage of permitting recycle of the dimethylamine without formation of a tarry mass. This has the consequence that the process can be carried out trouble-free, and in a manner which saves costs and energy.

Since the unconverted dimethylamine is recycled to the reaction and only the water of reaction arises as a waste product, no effluent problems and environmental problems arise.

EXAMPLE 1

Per hour, 900 kg of dimethylamine and 700 kg of water are warmed to 150° C and introduced into the mixing chamber 4. 250 kg/hour of ethylene chloride are admixed. The reaction mixture is passed through a reactor 5 where the reaction takes place at 100 bars and 180° C.

After the reaction, the reaction product is let down into a pressure column 8 at 10 bars, into which about 60 1/hour of 50% strength sodium hydroxide solution 6 are fed additionally. Excess dimethylamine is withdrawn at the top 9 and recycled. In a subsequent reactor 10, further sodium hydroxide solution is added to the bottom product of the pressure column 8 in order to completely liberate the amines from the hydrochlorides. The liberation of the amines by means of the sodium hydroxide solution is carried out at 125° C. Sodium chloride which crystallises out at this point is separated off continuously, while tetramethylethylenediamine, dimethylamine and water are passed as vapour, via a vapour pipe 12, to a column 14 under normal pressure.

In this column, the separation into a water/tetramethylethylenediamine mixture of low dimethylamine content (bottom product, boiling point: 95° – 96° C) and a water/tetramethylethylenediamine mixture which is supersaturated with dimethylamine (top product, boiling point: 60° – 75° C) is effected. The top condensate is fed back into the column, as reflux 16. The dimethylamine, which does not condense in the condenser is passed, together with the impurities, to an absorption system 17 in which the dimethylamine is treated with water and recycled to the input of the reaction zone 2. The impurities are not absorbed and are separated off at the top of the absorber 19. The bottom product, of low dimethylamine content, is separated in a further column 20 under normal pressure. A 68% strength azeotrope of tetramethylethylenediamine and water 21 is obtained as the top distillate. The bottom of this column contains the bulk of the water used in the reaction, but no tetramethylethylenediamine 22.

What is claimed is:

1. Process for the continuous preparation of tetramethylethylenediamine which comprises reacting 1,2-dichloroethane at a temperature between 130° and 200° C and under a pressure of 80–120 bar with an excess of dimethylamine in the continuous presence of water, liberating the amines in the reaction product by treatment with bases and separating unconverted dimethylamine, treating same with water and recycling it to the reaction.

2. Process of claim 1 wherein the reaction is carried out in the presence of 600 to 800 kg of water, relative to 800 to 1.00 kg of dimethylamine and 150 to 350 kg of ethylene chloride per hour.

3. Process of claim 1 wherein the reaction is carried out in the presence of 650 to 750 kg of water, relative to 850 to 950 kg of dimethylamine and 200 to 300 kg of ethylene chloride per hour.

4. Process of claim 1 wherein dimethylamine is separated as a vapor after the reaction is treated with water and the aqueous solution of the dimethylamine is recycled to the reaction.

5. Process of claim 1 wherein the reaction mixture is passed down into a column while adding concentrated aqueous alkali metal hydroxide solution thereto, and a product consisting of dimethylamine is withdrawn overhead and recycled to the reaction.

6. Process of claim 1 wherein the separation of the reaction product is effected by means of a column to give a bottom product consisting of tetramethylethylenediamine and water and a overhead product consisting of dimethylamine, water and tetramethylethylenediamine and the overhead product is separated, in a condenser, into a liquid phase consisting of dimethylamine, water and tetramethylethylenediamine which is fed as reflux into the column, and into a vapor phase essentially containing dimethylamine.

7. Process of claim 1 wherein after the separation of the reaction product the bottom product consisting of tetramethylethylenediamine and water is separated in a further column into a 68% strength azeotrope with water, as the overhead product, and a bottom product essentially containing water.

8. Process of claim 1 wherein 1,2-dichloroethane is reacted with dimethylamine in the presence of water at temperatures of 130° to 200° C and pressures of 80 to 120 bars, the reaction product consisting essentially of tetramethylethylenediamine, unconverted dimethylamine and water is passed down into a column, with addition of concentrated aqueous alkali metal hydroxide solution, the overhead product of this column, consisting of dimethylamine, is recycled to the reaction, the bottom product is again treated with a concentrated aqueous alkali metal hydroxide solution and passed into a further column in which a separation into a bottom product consisting of water and tetramethylethylenediamine and an overhead product consisting of dimethylamine, water and tetramethylethylenediamine is effected, and the latter overhead product is separated, in a condenser, into a liquid phase consisting of dimethylamine, water and tetramethylethylenediamine, which is fed as reflux into the column, and a vapor phase essentially containing dimethylamine.

* * * * *